United States Patent [19]

Nachtigal

[11] 3,976,765

[45] Aug. 24, 1976

[54] ANTIBACTERIAL ORAL PREPARATIONS

[75] Inventor: Julius Harvey Nachtigal, Colonia, N.J.

[73] Assignee: Colgate-Palmolive Company, New York, N.Y.

[22] Filed: Dec. 12, 1974

[21] Appl. No.: 531,889

Related U.S. Application Data

[63] Continuation-in-part of Ser. No. 411,723, Nov. 1, 1973, abandoned.

[52] U.S. Cl. .................................................. 424/54
[51] Int. Cl.² ........................................ A61K 7/22
[58] Field of Search .................................... 424/54

[56] References Cited
FOREIGN PATENTS OR APPLICATIONS

| 6,413,447 | 6/1965 | Netherlands | 424/54 |
| 825,577 | 12/1959 | United Kingdom | 424/54 |

OTHER PUBLICATIONS

Kirk–Othmer, Encyclopedia of Chemical Technology 2nd. Ed. vol. 2, published by Interscience Publishers, New York, p. 74, 1963.

Primary Examiner—Lewis Gotts
Assistant Examiner—Cary Owens
Attorney, Agent, or Firm—Robert L. Stone; Murray M. Grill; Herbert S. Sylvester

[57] ABSTRACT

Stable bis-biguanido hexane-containing oral products are disclosed which retain therapeutic activity against plaque and breath odor and concurrently possess desirable foaming properties. The oral products contain polyoxyethylene-polyoxypropylene nonionic surfactant in combination with a foam booster which is a long-chain tertiary amine oxide of $C_{10}$–$C_{18}$ chain length or monoethanolamide of a fatty acid having from 10 to 18 carbon atoms.

16 Claims, No Drawings

ANTIBACTERIAL ORAL PREPARATIONS

This application is a continuation-in-part of Ser. No. 411,723, filed Nov. 1, 1973, and now abandoned.

BACKGROUND OF THE INVENTION

This invention relates to oral compositions and, more particularly, to stable oral compositions containing bis-biguanido hexanes which have acceptable foaming properties.

Bis-biguanido hexanes, and particularly 1,6-di-(p-chlorophenyl biguanido) hexane (also known as chlorhexidine) and 1,6-bis(2-ethylhexyl biguanido) hexane are known to possess highly desirable effects in inhibiting the growth of many microorganisms such as *Lactobacillus acidophilus odontolyticus* and *Streptococcus mutans*. Additionally, the bis-biguanido hexanes have been found to be effective in preventing the formation of dental plaque, calculus, gingivitis, and mouth odor.

However, chemical interactions between cationic therapeutic agents such as bis-biguanido hexanes and conventional anionic detergents have presented a formidable problem in formulating oral products. It has been demonstrated that the presence of certain anionic detergents will considerably diminish the antibacterial effectiveness of bis-biguanido hexanes such as chlorohexidine and its salts in conventional oral preparations. Furthermore, despite the suitability of a number of nonionic surfactants with regard to therapeutic compatability, the foaming properties rendered to the oral preparation are still not comparable to that of an anionic surfactant. Foaming oral preparations are preferred by consumers over nonfoaming oral products.

SUMMARY OF THE INVENTION

It has been discovered that the use of polyoxyethylene-polyoxypropylene nonionic surfactants in combination with certain foam stabilizing materials renders foaming properties to the oral compositions comparable to anionic-containing oral preparations. Oral preparations with acceptable foaming properties may be formulated comprising a nonionic surfactant in combination with a suitable foam booster.

The preferred foam boosters are particularly applicable for incorporation into therapeutic oral preparations, specifically those oral preparations containing cationic agents such as chlorhexidine. These foam boosters allow retention of therapeutic activity of chlorhexidine-type agents normally not found using conventional anionic detergent systems.

The foam boosters are long-chain alkyl dimethyl amine oxides wherein the alkyl group has from about 10 to about 18 carbon atoms. Alternatively, monoethanolamides of $C_{10}$–$C_{18}$ aliphatic fatty acids may also be used as foam boosters in the instant invention. The oral product typically contains at least about 0.03%, say about 0.1–3% by weight of the foam booster, preferably about 0.5–2%.

Any nontoxic, antibacterial, water-soluble salt of the bis-biguanido hexanes may be employed in the practice of the instant invention. Specific examples thereof include water-soluble salts of 1,6-di(p-chlorophenyl biguanido) hexane and 1,6-bis(2-ethylhexyl biguanido) hexane. The preferred acid addition salts are the gluconate, acetate, fluoride, dihydrogen fluoride, dihydrogen chloride, and the like. The salts of 1,6-bis(2-ethylhexyl biguanido) hexane are more soluble in lower alcohols such as ethanol than in water, and are thus suitable for use in mouth rinses having fairly high alcohol content. For the purposes herein "water soluble" means sufficiently soluble to provide at least 0.0015% by weight of the free agent to the solution.

The antimicrobial agent is employed in amounts such that the oral preparation contains between about 0.0015% and about 15% by weight of the agent. Typically, the finished oral product contains about 0.001 to about 5.0% by weight, preferably about 0.01 to 5% by weight, and most preferably about 0.05% to 1.0% by weight of the agent. These amounts refer to the quantity of the free base form of the agent.

The oral preparations of the present invention may take the form of any preparation for human use designed for applications to and/or care of the oral cavity. Such preparations include toothpastes and dental creams, toothpowders, mouth rinses, and the like.

In certain forms of the invention the oral preparation may be substantially liquid in character, such as a mouth rinse. In such a preparation the vehicle is typically a water-alcohol mixture. Generally, the ratio of water to alcohol is in the range of about 1:1 to about 20:1, preferably 3:1 to 20:1, and most preferably about 17:3, by weight. The total amount of water-alcohol mixture in this type of preparation is typically in the range of from about 70% to about 99.9% by weight of the preparation, the pH of such liquid preparations is generally in the range of from about 4.5 to about 9, and typically from about 5.5 to about 8.

In certain other forms of this invention, the oral preparation may be substantially solid or pasty in character, such as a toothpowder, or a toothpaste or dental cream. The vehicle typically contains a dentally acceptable, substantially water-insoluble polishing agent, a liquid which may be water or a humectant, a gelling agent, and flavoring oil. It may also include additional components such as compatible synthetic organic surface-active agents (which may be anionic, nonionic, ampholytic, or cationic in nature), additional antibacterial agents, sweetener, dentally beneficial fluorine-containing compounds, an ion-suppressing agent as well as coloring or whitening agents, preservatives, silicones, chlorophyll compounds, ammoniated compounds, and the like.

Any suitable substantially water-insoluble dentally acceptable polishing agent may be employed in the preparation of dentifrice compositions, such as toothpastes or creams and the like, in accordance with the present invention. There is a relatively large number of such materials known in the art. Representative agents include, for example, dicalcium phosphate, dimagnesium orthophosphate, tricalcium phosphate, insoluble sodium metaphosphate, aluminum hydroxide, crystalline silica, magnesium carbonate, calcium carbonate, calcium pyrophosphate, bentonite, etc., including suitable mixtures thereof. It is often desired to use the substantially water-insoluble phosphate salts as the polishing agents, and, more particularly, insoluble sodium metaphosphate. In dentifrices containing 1,6-di-(p-chlorophenyl biguanido) hexane, aluminum hydroxide, such as the hydrated alumina sold by Alcoa as C333, and crystalline silica polishing agents are also highly desirable. Since polishing agents such as insoluble sodium metaphosphate and calcium and magnesium phosphates contain a soluble portion, the amounts in which they are used should not provide more than about 2% by weight of phosphate ion to the dentifrice.

The polishing agent content is variable, but will generally be up to about 75% by weight of the total composition, typically about 20–75%.

In dentifrice vehicles of formulations such as toothpastes and dental creams, liquids and solids should necessarily be proportioned to form a creamy or gelled mass of desired consistency which is extrudable from an aerosol container or a collapsible, e.g., aluminum or lead, tube. In general, the liquids in the dental cream will comprise chiefly water, glycerine, aqueous solutions of sorbitol, propylene glycol, polyethylene glycol 400, etc., including suitable mixtures thereof. It is advantageous usually to use a mixture of both water and a humectant or binder such as glycerine or sorbitol. The total liquid content will generally be about 20–75% by weight of the formulation. It is preferred to use also a gelling agent in dental creams such as the natural and synthetic gums and gum-like materials, e.g., Irish moss, gum tragacanth, methyl cellulose, hydroxyethyl cellulose, sodium carboxymethyl cellulose, polyvinylprroli-done and starch, usually in an amount up to about 10%, and preferably about 0.2–5% of the formulation. The preferred gelling agents are sodium carboxymethyl cellulose, methyl cellulose and hydroxyethyl cellulose. If sodium carboxymethyl cellulose is employed, preferably the dentifrices are formed in accordance with the technique described in U.S. Pat. No. 3,842,168 of Daniel Colodney granted Oct. 15, 1974 and U.S. Pat. No. 3,843,779 of James Norfleet granted Oct. 22, 1974.

In the preparation of toothpowders, it is usually sufficient to admix mechanically, e.g., by milling, the various solid ingredients, in appropriate quantities and particle sizes.

Organic surface-active agents, used in the compositions of the present invention to achieve increased prophylactic action, assist in achieving thorough and complete dispersion of the instant compositions throughout the oral cavity, and render the instant compositions more cosmetically acceptable. The surface-active agent employed is a detersive material which imparts to the preparation detersive properties and is compatible with the antibacterial activity of the bisbiguanido hexane.

Suitable surfactants for use in the present invention are condensates of ethylene oxide with propylene oxide condensates of propylene glycol (available under the trademark "Pluronic").

Pluronic nonionic surfactants include solid, paste and liquid materials and have the formula: HO(CH$_2$CH$_2$O)$_a$(CH(CH$_3$)CH$_2$O)$_b$-(CH$_2$CH$_2$O)$_c$H wherein $a$, $b$ and $c$ are integers reflecting the respective blocks of said polymer. These materials are generally described in terms of the percent by weight of polyoxyethylene moiety and the molecular weight of the polyoxypropylene moiety. The following table presents commercially available Pluronic surfactants:

Table

| Pluronic | % by weight Polyoxyethylene | Polyoxypropylene Molecular Weight |
|---|---|---|
| L 31 | 10 | 950 |
| L 61 | 10 | 1750 |
| L 81 | 10 | 2250 |
| L101 | 10 | 3250 |
| L121 | 10 | 4000 |
| L 42 | 20 | 1200 |
| L 62 | 20 | 1750 |
| L 72 | 20 | 2050 |
| L 92 | 20 | 2750 |
| L122 | 20 | 4000 |
| L 43 | 30 | 1200 |

Table-continued

| Pluronic | % by weight Polyoxyethylene | Polyoxypropylene Molecular Weight |
|---|---|---|
| L 63 | 30 | 1750 |
| P103 | 30 | 3250 |
| P123 | 30 | 4000 |
| L 44 | 40 | 1200 |
| L 64 | 40 | 1750 |
| P 84 | 40 | 2250 |
| P 94 | 40 | 2750 |
| P104 | 40 | 3250 |
| L 35 | 50 | 950 |
| P 65 | 50 | 1750 |
| P 75 | 50 | 2050 |
| P 85 | 50 | 2250 |
| P105 | 50 | 3250 |
| F 77 | 70 | 2050 |
| F 87 | 70 | 2250 |
| F 38 | 80 | 950 |
| F 68 | 80 | 1750 |
| F 88 | 80 | 2250 |
| F 98 | 80 | 2750 |
| F108 | 80 | 3250 |

In the naming of Pluronic materials, "L" indicates a liquid "P" indicates a paste and "F" indicates a solid flake material. The preferred Pluronic material is F 108.

It is preferred to use at least about 0.05% typically at least about 0.15% by weight of the foregoing surface-active materials in the instant oral preparations. They may be used in amount up to about 12% and preferably up to about 5% by weight. The weight ratio of surfactant to foam boosters may range from about 3:2 to about 4:1. The preferred ratio is 19:6.

Amine oxide foam boosters include Conco XA-M, a cationic myristyl dimethylamine oxide; Chemadox 300, an amphoteric amine oxide; Ammonyx LO, a nonionic n-decyl dimethylamine oxide. Cetyl dimethylamine oxide is another amine oxide which can be employed. Conco XA-M is preferred.

The monoethanolamide foam boosters include lauric myristic monoethanolamide as well as decyl monoethanol amide and cetyl monoethanol amide. The monoethanol amide available as Monoamide 716 is desirable.

Various other materials may be incorporated in the oral preparations of this invention. Examples thereof are coloring or whitening agents, preservatives, silicones, chlorophyll compounds, ammoniated materials such as urea diammonium phosphate and mixtures thereof, and other constituents. These adjuvants are incorporated in the instant compositions in amounts which do not substantially adversely affect the properties and characteristics desired and are selected and used in proper amount depending upon the particular type of preparation involved. For example, ammoniated materials such as urea, diammonium phosphate and mixtures thereof, when present, are typically employed in an amount of about 1 to 2% by weight.

In addition to bis-biguanido hexanes, dentifrices in accordance with this invention may include additional cationic antibacterial agents such as:

N$^1$-(4-chlorobenzyl)-N$^5$-(2,4-dichlorobenzyl)biguanide
p-chlorophenyl biguanide.
4-chlorobenzhydryl biguanide;
4-chlorobenzhydrylguanylurea;
N-3-lauroxypropyl-N$^5$-p-chlorobenzylbiguanide;
1-(lauryldimethylammonium)-8-(p-chlorobenzyl-dimethylammonium octane dichloride;

5,6-dichloro-2-guanidinobenzimidazole;
N$^1$-p-chlorophenyl-N$^5$-laurylbiguanide;
5-amino-1,3-bis(2-ethylhexyl)-5-methylhexahydropyrimidine;

and their nontoxic acid addition salts such as the gluconate and acetate. The total amount of such agents including 1,6-di-(p-chlorophenyl biguanido) hexane is typically about 0.050 to about 5% by weight.

The dentifrice vehicle of the instant invention contains a flavoring oil and may also contain a sweetening agent. Examples of suitable flavoring oil include oils of spearmint, peppermint, wintergreen, sassafras, clove, sage, eucalyptus, marjoram, cinnamon, lemon and orange, as well as methylsalicylate. Suitable sweetening agents include sucrose, lactose, maltose, sorbitol, sodium cyclamate, perillartine and saccharin. Suitably, flavor alone or together with a sweetening agent may totally comprise from about 0.01 to 5% or more of the compositions of the instant invention.

The compositions of the present invention suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride (SnF$_2$.KF), sodium hexafluorostannate, stannous chlorofluoride, sodium fluorozirconate, and sodium monofluorophosphate. These material, which dissociate or release fluorine-containing ions in water, suitably may be present in an effective but nontoxic amount, usually within the range of about 0.01 to 1% by weight of the water soluble fluorine content thereof.

The dentifrices should have a pH practicable for use. The pH range of about 5 to 9, preferably about 6–7, is considered the most practicable for use. Where reference is made to pH herein, it is intended that such pH determination be made on the dentifrice directly.

In the event the dentifrice vehicle contains as polishing agent a water-insoluble calcium or magnesium salt, there may be employed also various calcium and magnesium ion suppression agents for adjustment of physical properties of the composition. Suitable agents are the water-soluble inorganic polyphosphate salts, such as tetrasodium pyrophosphate or disodium diacid pyrophosphate, with the partially neutralized or acid polyphosphates preferred. In general, such compounds will be a minor amount or proportion of the formulation. The precise amount will vary depending upon the specific formulation, such as the physical characteristics of the dental cream, but will usually be from about 0.1% to about 2% by weight.

In accordance with certain additional aspects of the invention it is particularly desirable that the oral product contain as an antioxidant or reducing agent which inhibits formation of dental stain, dihydrocoumarin, or tri-hydroxylated benzoic acid and its esters. These reducing agents are present in compounds of the present invention in amounts of about 0.001% to 10% by weight, and preferably from about 0.01% to 5% by weight.

Dihydrocoumarin, otherwise known as benzodihydropyrone, and more commonly referred to as melilotin, has been shown to be compatible with chlorhexidine to the extent that 70% chemical activity is assured through 9 weeks accelerated aging at 120°F. Additionally, melilotin has demonstrated in vitro effectiveness in inhibiting chlorhexidine-tea stain formation and HOCl oxidation of chlorhexidine.

Tri-hydroxylated (i.e., phenolic) benzoic acid and its lower alkyl (C$_1$ to C$_4$ carbon atoms) esters are also effective in stabilizing the oral preparations while inhibiting dental stain formation. Among the most effective of these tri-hydroxylated benzoic acid esters are 3,4,5-trihydroxybenzoic acid (more commonly known as gallic acid) and its propyl ester, propyl gallate.

DESCRIPTION OF THE PREFERRED EMBODIMENTS

The following specific examples are further illustrative of the nature of the present invention, but it is to be understood that the invention is not limited thereto.

EXAMPLE I

In order to demonstrate the retention of antibacterial activity in compositions containing the foam boosters according to the present invention, 5% aqueous solutions of chlorhexidine were formulated using 2% of a foam booster in each solution. The solutions were subjected to accelerated aging at 120°F. for 9 weeks, which process simulates an acceptable shelf life. The results are tabulated below:

| Foam Booster | Concentration | % Activity Recovered After Aging at 120°F. | | | |
|---|---|---|---|---|---|
| | | Initial | 3 wks. | 6 wks. | 9 wks. |
| Conco XA-M[a] | 2% | 103 | 87 | 86 | 97 |
| Chemadox 330[b] | 2% | 101 | 93 | 85 | 104 |
| Ammonyx LO[c] | 2% | 102 | 91 | 96 | 109 |
| Barlox 10S[d] | 2% | 110 | 100 | 80 | 122 |

[a]cationic myristyl dimethylamine oxide
[b]amphoteric amine oxide
[c]nonionic lauryl dimethylamine oxide
[d]nonionic n-decyl dimethylamine oxide The above results illustrate the retention of activity of a combination of chlorhexidine with the foam boosters of the present invention. The increase in % of activity at nine weeks appears to be the result of an experimental error.

EXAMPLE II

A convention dentifrice containing anionic surfactant alone was compared with dentifrices containing nonionic surfactant plus a foam booster for foam volume. The results are tabulated below:

| Detergent | Foam Booster | Foam Volume (cm.) |
|---|---|---|
| Sodium lauroyl sarcosinate (control) | None | 4.3 |
| Pluronic F-108* | None | 1.3 |
| Pluronic F-108 | Conco XA-M | 4.0 |

*condensate of ethylene oxide with a hydrophobic base formed by condensing propylene oxide with propylene glycol The ratio of Pluronic F-108 to Conco XA-M is 19:6 by weight.

This example illustrates that polyoxyethylene-polyoxypropylene nonionic surfactants combined with the foam boosters of the present invention have a foaming activity approaching that of the anionic surfactants conventionally used in oral formulations. Dentifrice formulations containing the above nonionic species in combination with chlorhexidine have aged satisfactorily from a cosmetic point of view.

Similarly, improved foam boosting and desirable product is obtained when the foam booster is lauric myristic monoethanolamide.

The above-described invention relates to the successful combination of bis-biguanido hexanes with a surfactant combination shown effective in boosting foam without reacting adversely with the active ingredient.

What is claimed is:

1. An oral composition comprising a bis-biguanido hexane in amount of about 0.001–5% by weight based on the free base thereof about 0.05–12% by weight of a nonionic polyoxyethylene-polyoxypropylene block copolymer surfactant, a foam booster selected from the group consisting of alkyl dimethyl amine oxides wherein the alkyl group contains from about 10 to about 18 carbon atoms and monoethanolamides of fatty acids having from about 10 to about 18 carbon atoms, the ratio of said nonionic surfactant to said foam booster being from about 3:2 to about 4:1 by weight, and a suitable vehicle.

2. The oral composition of claim 1 wherein said bis-biguanido hexane is selected from the group consisting of 1,6-di-(p-chlorophenyl biguanido) hexane and 1,6-bis-(2-ethylhexyl-biguanido) hexane.

3. The oral composition of claim 1 wherein a substantially water-insoluble polishing agent is present and said oral composition is a dentifrice.

4. The oral composition of claim 3 wherein said substantially water-insoluble polishing agent is a phosphate salt.

5. The oral composition of claim 1 wherein the vehicle is a water-alcohol mixture and said composition is a mouthwash.

6. The oral composition of claim 1 wherein the ratio of the nonionic surfactant to the foam booster is about 19:6 by weight.

7. The oral composition of claim 1 wherein the foam booster is an alkyl dimethyl amine oxide having an alkyl group of from 10 to 18 carbon atoms.

8. The oral composition of claim 7 wherein the foam booster is myristyl dimethyl amine oxide.

9. The oral composition of claim 7 wherein the foam booster is lauryl dimethyl amine oxide.

10. The oral composition of claim 7 wherein the foam booster is n-decyl dimethyl amine oxide.

11. The oral composition of claim 1 wherein the foam booster is a monoethanolamide of a fatty acid having from 10 to 18 carbon atoms.

12. The oral composition of claim 11 wherein the foam booster is monoethanolamide of lauric acid and myristic acid.

13. The oral composition of claim 1 wherein the block copolymer contains about 80% by weight of polyoxyethylene moiety and the molecular weight of the polyoxypropylene moiety is about 3250.

14. The oral composition of claim 13 wherein the foam booster is myristyl dimethyl amine oxide.

15. The oral composition of claim 14 wherein the ratio of the block copolymer to myristyl dimethyl amine oxide is about 19:6.

16. The oral composition of claim 1 wherein said block copolymer surfactant is present in amount of about 0.05 – 5% by weight.

* * * * *